United States Patent
Watanabe

(10) Patent No.: US 9,844,342 B2
(45) Date of Patent: Dec. 19, 2017

(54) SENSOR AND SHAPE RETAINER

(71) Applicant: NIHON KOHDEN CORPORATION, Tokyo (JP)

(72) Inventor: Nobuyoshi Watanabe, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 442 days.

(21) Appl. No.: 14/489,532

(22) Filed: Sep. 18, 2014

(65) Prior Publication Data

US 2015/0105639 A1    Apr. 16, 2015

(30) Foreign Application Priority Data

Oct. 10, 2013  (JP) .................................. 2013-212863

(51) Int. Cl.
| | |
|---|---|
| *A61B 5/00* | (2006.01) |
| *A61B 5/1455* | (2006.01) |
| *A61B 5/0205* | (2006.01) |
| *A61B 5/024* | (2006.01) |

(52) U.S. Cl.
CPC .......... *A61B 5/6838* (2013.01); *A61B 5/0205* (2013.01); *A61B 5/1455* (2013.01); *A61B 5/14551* (2013.01); *A61B 5/6816* (2013.01); *A61B 5/6826* (2013.01); *A61B 5/02416* (2013.01); *A61B 5/02438* (2013.01); *A61B 2562/221* (2013.01)

(58) Field of Classification Search
CPC ... A61B 5/6816; A61B 5/6826; A61B 5/6838; A61B 5/6839; A61B 5/1455; A61B 5/0205

See application file for complete search history.

(56) References Cited

U.S. PATENT DOCUMENTS

| | | | | |
|---|---|---|---|---|
| 5,386,489 | A | * | 1/1995 | Stokes .................. G02B 6/403 264/154 |
| 5,461,200 | A | | 10/1995 | Norcia |
| 6,874,908 | B2 | * | 4/2005 | Sharrah ................. F21L 4/027 362/119 |
| 2004/0054291 | A1 | | 3/2004 | Schulz et al. |
| 2010/0256460 | A1 | | 10/2010 | Haven et al. |
| 2012/0253159 | A1 | | 10/2012 | Medina et al. |

(Continued)

FOREIGN PATENT DOCUMENTS

| | | |
|---|---|---|
| JP | H06-070395 U | 9/1994 |
| JP | 7-28502 U | 5/1995 |

(Continued)

OTHER PUBLICATIONS

The extended European Search Report for the related European Patent Application No. 14187000.6 dated Mar. 3, 2015.

(Continued)

*Primary Examiner* — Eric Winakur
(74) *Attorney, Agent, or Firm* — Pearne & Gordon LLP

(57) ABSTRACT

A sensor attached to a living body includes a sensor body that outputs a signal corresponding to biological information, and a cable that is connected to a sensor body and transmits the signal. The cable has a first portion having a first flexibility and a second portion having a second flexibility lower than the first flexibility. The second flexibility enables the second portion to be bent, and is able to retain a shape of the second portion in a bent state.

3 Claims, 8 Drawing Sheets

(56) References Cited

U.S. PATENT DOCUMENTS

2013/0010997 A1  1/2013  Tanaka et al.
2015/0041173 A1* 2/2015  Chin .................... B65H 75/362
                                                            174/69

FOREIGN PATENT DOCUMENTS

| JP | H08-079875 A   | 3/1996  |
| JP | 2004-180252 A  | 6/2004  |
| JP | 2009-194790 A  | 8/2009  |
| JP | 2012-244515 A  | 12/2012 |
| JP | 2013-012396 A  | 1/2013  |
| JP | 2013-013540 A  | 1/2013  |
| WO | 2009/147370 A1 | 12/2009 |

OTHER PUBLICATIONS

Office Action issued in Patent Application No. JP 2013-212863 dated Feb. 7, 2017.

* cited by examiner

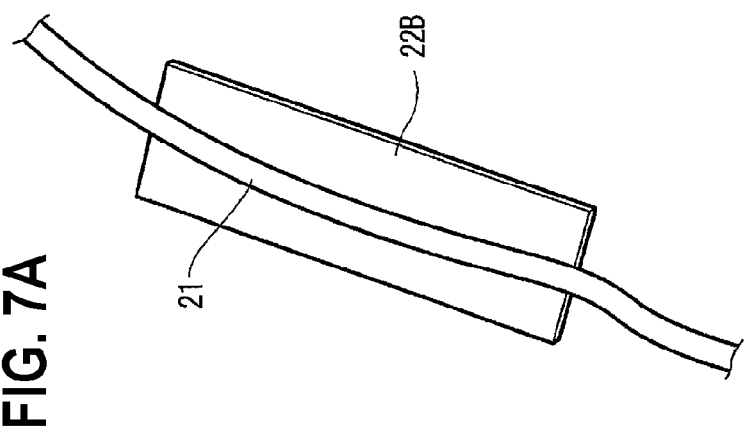
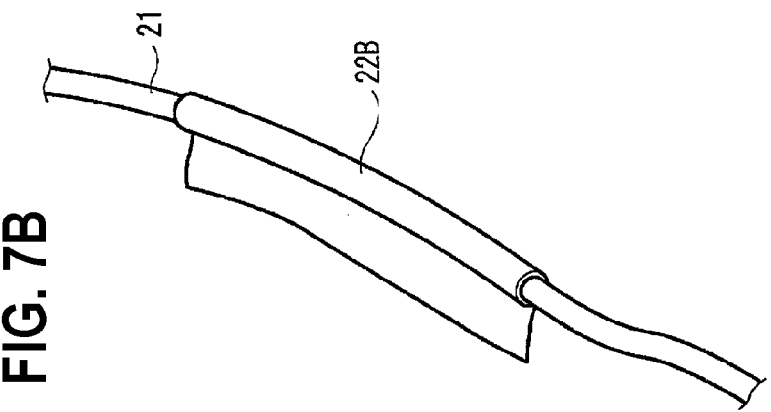
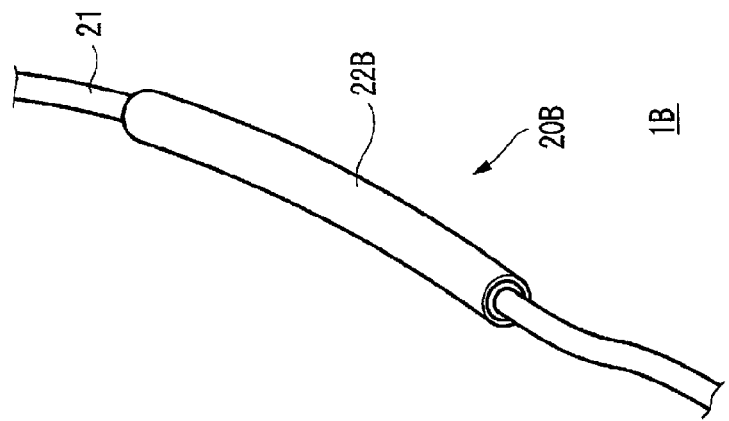

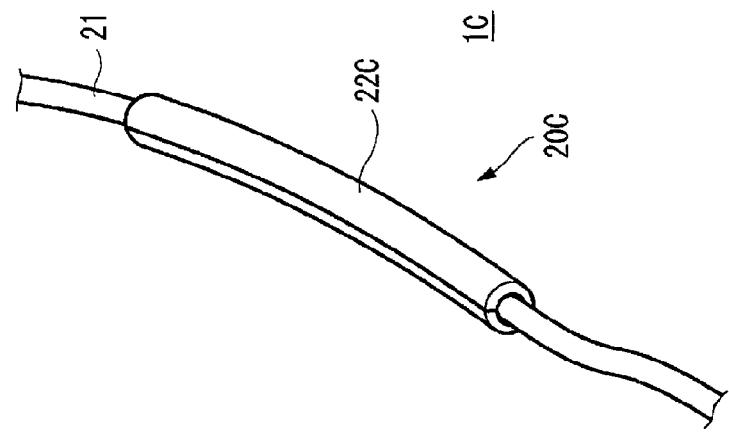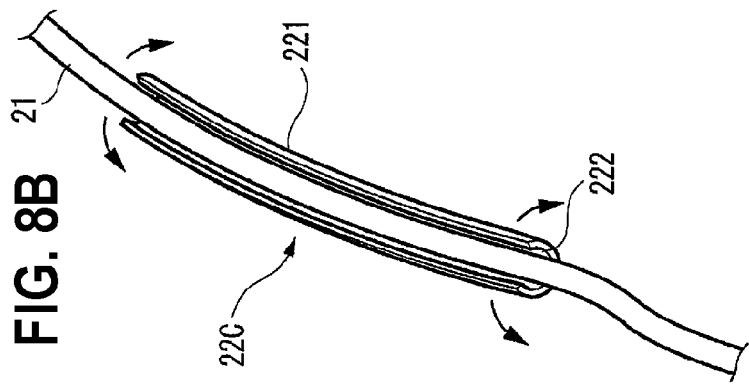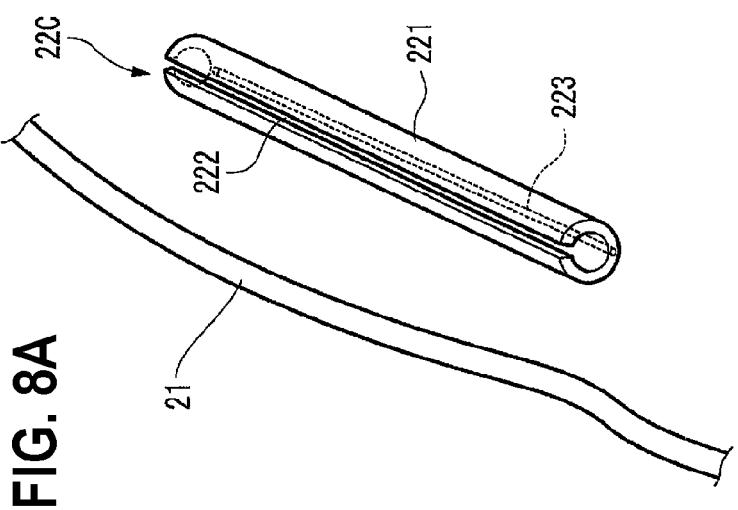

SENSOR AND SHAPE RETAINER

CROSS REFERENCE TO RELATED APPLICATION

This application is based on Japanese Patent Applications No. 2013-212863 filed on Oct. 10, 2013, the contents of which are incorporated herein by reference.

BACKGROUND

The presently disclosed subject matter relates to a sensor which is attached to a living body to detect biological information, and also to a shape retainer which is attached to a cable for transmitting a signal corresponding to the biological information.

When a cable connected to a sensor attached to a living body (subject) is in a freely swingable state, noises may be caused to enter a signal transmitted through the cable. Therefore, a procedure of securing the cable to the skin of the subject with an adhesive tape is sometimes performed. Alternatively, a sensor is sometimes used in which a securing device having a predetermined shape is attached to the cable (for example, see JP-UM-A-7-028502). The securing device is secured to a part of the body of the subject to prevent the cable from swinging.

SUMMARY

In the case where the subject has sensitive skin, when a cable is secured to the skin with an adhesive tape, there is a possibility that the skin may become inflamed. Therefore, positions where securing with an adhesive tape may be performed are limited. The securing device disclosed in JP-UM-A-7-028502 has the predetermined shape corresponding to the attaching place of the body. Therefore, the degree of freedom of selection of the place where the cable is to be secured is low.

Therefore, an object of the presently disclosed subject matter is to provide a technique for enhancing the degree of freedom of selection of the place where a cable of a sensor for detecting biological information is to be secured.

In order to attain the object, a first aspect of the presently disclosed subject matter is a sensor which is attached to a living body, wherein the sensor includes:

a sensor body configured to output a signal corresponding to biological information; and a cable configured to be connected to the sensor body and to transmit the signal, the cable has a first portion having a first flexibility, and a second portion having a second flexibility which is lower than the first flexibility, and the second flexibility enables the second portion to be bent and to retain a shape which is in a bent state.

According to the configuration, the second portion can be freely bent based on the second flexibility, and therefore can be deformed so as to extend along a desired portion of the body of the subject. Moreover, the second portion can be deformed so as to extend along the body shape which varies from subject to subject. As a result, the cable can be secured to a desired portion of the body of the subject. Furthermore, the second portion can self-retain the bent shape based on the second flexibility, and therefore an adhesive tape or an additional securing device is not required in the securement. Consequently, it is possible to enhance the degree of freedom of selection of the place where the cable of the sensor for detecting biological information is to be secured.

The second portion may include large-diameter parts having a first maximum diameter, and small-diameter parts having a second maximum diameter which is smaller than the first maximum diameter.

Usually, a body portion of the subject to which the second portion is attached has irregular convex and concave portions. According to the configuration, difference in size formed between the large-diameter parts and the small-diameter parts can be easily caught by the irregular convex and concave portions, so that the cable can be secured more surely to a body portion of the subject. Therefore, it is possible to enhance the degree of freedom of selection of the place where the cable of the sensor for detecting biological information is to be secured.

The large-diameter parts may be formed by a material having a third flexibility which is higher than the first flexibility.

According to the configuration, even when the difference in size formed between the large-diameter parts and the small-diameter parts contacts with a body portion of the subject, the burden on the skin of the subject can be suppressed. Therefore, it is possible to enhance the degree of freedom of selection of the place where the cable of the sensor for detecting biological information is to be secured.

The second portion may be attachable to and detachable from the first portion.

The second portion also may have a core line embedded in the whole length of the second portion in a longitudinal direction of the second portion.

According to the configuration, in accordance with the shape of a body portion of the subject to which the cable is to be secured, a portion of the cable in which a bent state must be retained can be arbitrarily set. Therefore, it is possible to enhance the degree of freedom of selection of the place where the cable of the sensor for detecting biological information is to be secured.

In this case, the second portion functions as a shape retainer that is attached to the cable of the sensor which is attached to a living body to detect biological information, and that retains the shape of the cable to a desired state.

In order to attain the object, therefore, a second aspect of the presently disclosed subject matter is a shape retainer attached to a cable for transmitting a signal, wherein the shape retainer has a second flexibility which is lower than a first flexibility of the cable, and the second flexibility allows the retainer to be bent and to retain a shape which is in a bent state.

The shape retainer can be attached to an adequate cable for transmitting a signal. In a state where a cable of an electronic apparatus is bent, and secured to a desired place, for example, the shape retainer can retain the bent shape.

BRIEF DESCRIPTION OF DRAWINGS

FIGS. 7A to 7C are perspective views illustrating a part of a sensor of a third embodiment of the presently disclosed subject matter.

FIGS. 8A to 8C are perspective views illustrating a part of a sensor of a fourth embodiment of the presently disclosed subject matter.

DETAILED DESCRIPTION OF EMBODIMENTS

Figure 1:
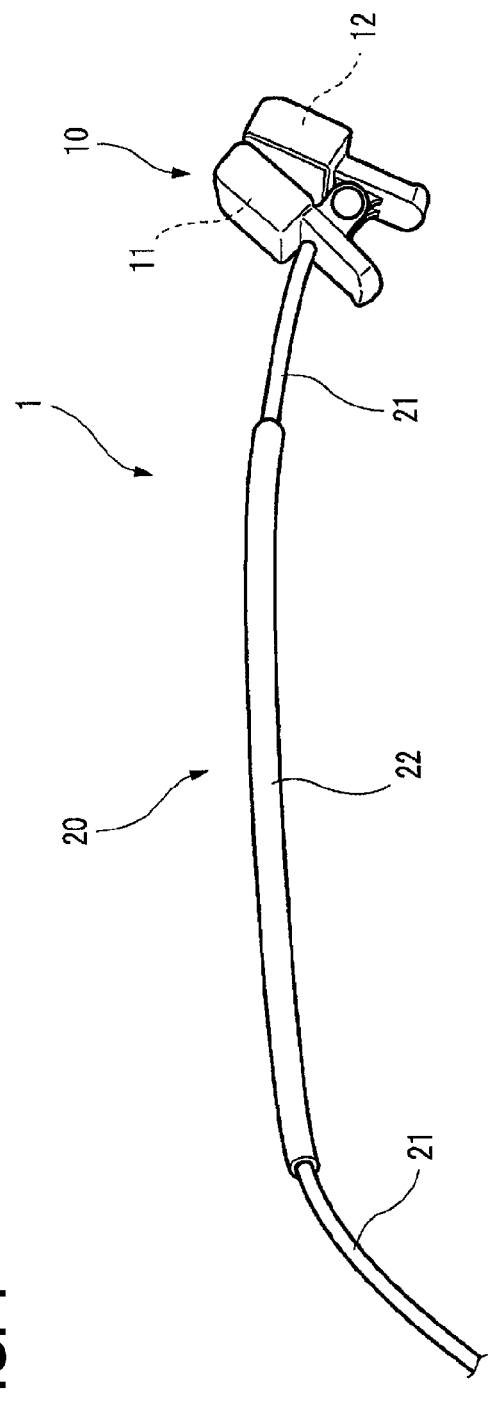
FIG. 1 is a perspective view illustrating a sensor of a first embodiment of the presently disclosed subject matter.

Hereinafter, embodiments of the presently disclosed subject matter will be described in detail with reference to the accompanying drawings. In the drawings which will be used in the following description, the scale is adequately changed in order to draw components in a recognizable size.

FIG. 1 is a perspective view illustrating a sensor 1 of a first embodiment of the presently disclosed subject matter. The sensor 1 attached to a living body (subject) can include a sensor body 10 and a cable 20. The sensor 1 is used as a probe of a pulse oximeter.

The sensor body 10 has a clip-like shape, and is configured so as to be able to clamp a portion (fingertip, earlobe, or the like) of the body of the subject. The sensor body 10 can include a light emitter 11 and a light detector 12. The light emitter 11 is configured so as to emit a red light and an infrared light. The light detector 12 is configured so as to output signals corresponding to the intensities of the light which have been passed through the body part of the subject clamped by the sensor body 10.

In hemoglobin in blood, absorbances of a red light and an infrared light are different from each other depending on presence or absence of oxygenation. When the intensities of the light detected by the light detector 12 are analyzed, therefore, it is possible to measure the arterial oxygen saturation (SpO2). When the pulse wave component due to the pulsation of the heart is detected, it is possible to measure the heart rate. Namely, the sensor body 10 outputs signals corresponding respectively to the SpO2 and heart rate which are examples of biological information.

The cable 20 transmits the signals output from the light detector 12 to the pulse oximeter which is not shown. The pulse oximeter measures the SpO2 and heart rate which are described above, based on the transmitted signals.

The cable 20 can include a first portion 21 and a second portion 22. One end of the first portion 21 is connected to the light detector 12, and the other end of the first portion 21 is connected to the pulse oximeter.

The first portion 21 has a first flexibility. The first flexibility is at a degree which enables the first portion to be bent, and which disables the first portion to retain the shape in a bent state.

The second portion 22 is disposed so as to partly cover the first portion 21. The second portion 22 has a second flexibility. The second flexibility is lower than the first flexibility. The second flexibility is at a degree which enables the second portion to be bent, and which enables the second portion to retain the shape in a bent state.

Figure 2:
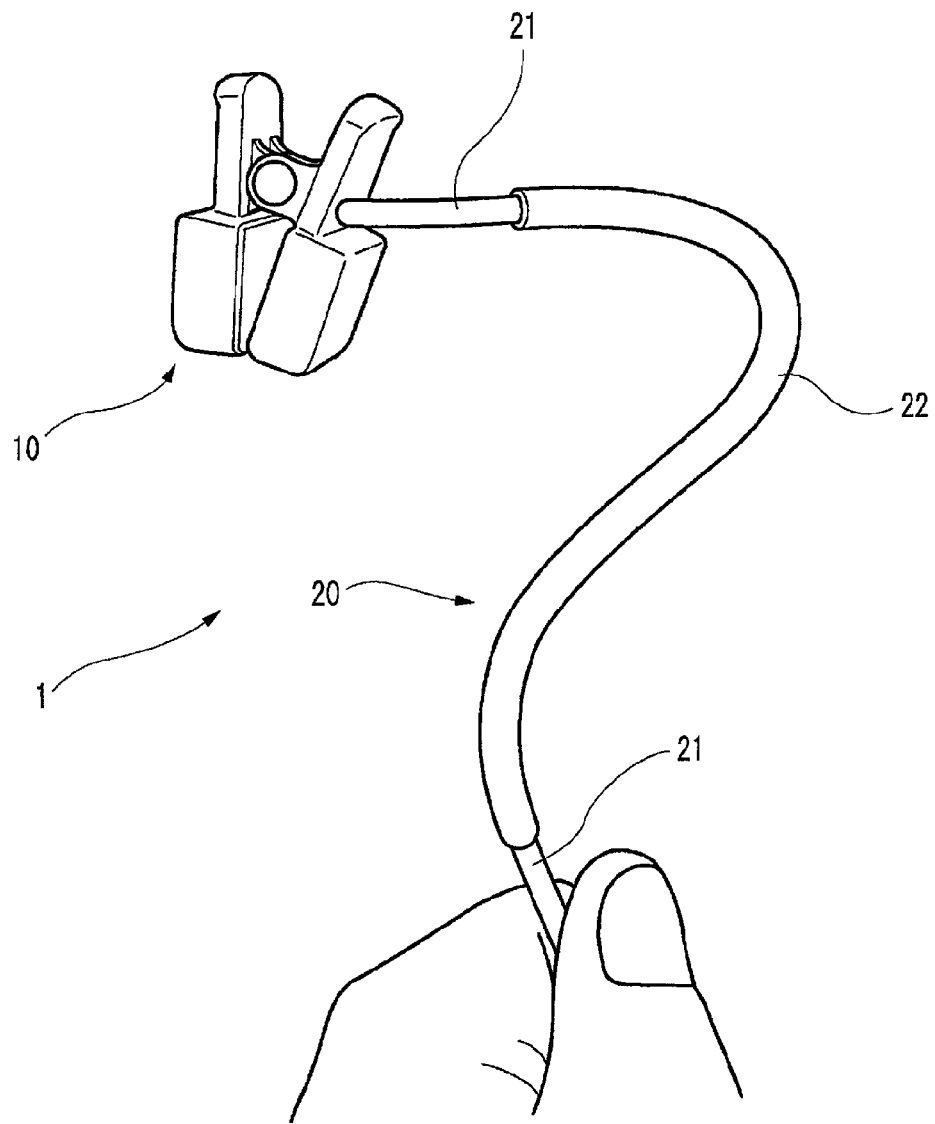
FIG. 2 is a perspective view illustrating a state where a cable of the sensor of FIG. 1 is deformed.

FIG. 2 is a perspective view illustrating a state where the cable 20 having the above-described configuration is deformed. The figure illustrates the state where the second portion 22 is bent to exhibit a desired shape, and a part immediately below one end of the second portion 22 is nipped in fingertips so that the sensor body 10 is located above the fingertips.

The second portion 22 retains the shape of the bent state based on the above-described second flexibility. Therefore, the cable 20 in the self-supported state supports the sensor body 10 in the illustrated position. If the cable is configured only by the first portion 21, the cable cannot support the weight of the sensor body 10 based on the first flexibility, and is downwardly bent.

Figure 3:
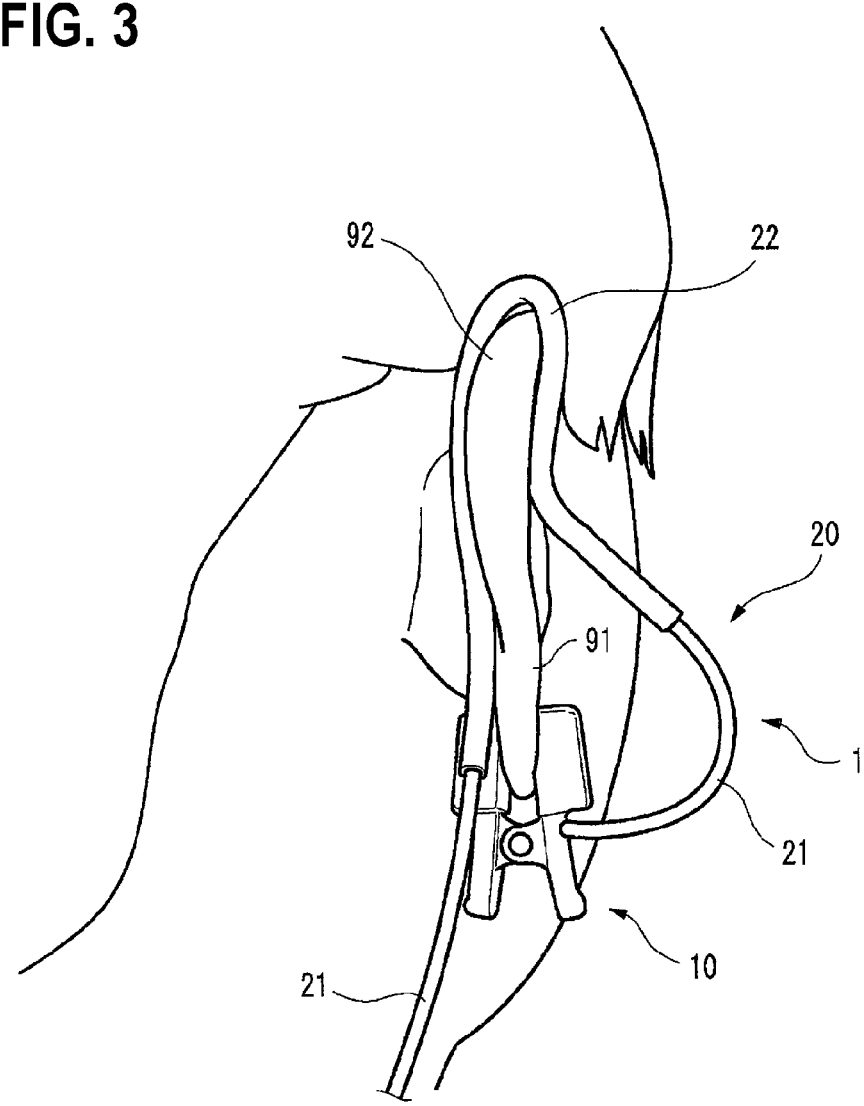
FIG. 3 is a perspective view illustrating a state where the sensor of FIG. 1 is attached to the ear of the subject.

FIG. 3 is a perspective view showing a state where the sensor 1 having the above-described configuration is attached to the ear of the subject. The sensor body 10 clamps the earlobe 91 of the subject. The second portion 22 of the cable 20 goes around an upper portion 92 of the ear. The second portion 22 is bent and deformed into a shape which extends along the upper portion 92 of the ear. The second portion 22 can retain the shape in the bent state, and therefore the state where the portion is fitted to the upper portion 92 of the ear is maintained.

The second portion 22 can be freely bent based on the second flexibility, and therefore deformed so as to extend along a desired portion of the body of the subject. Moreover, the second portion 22 can be deformed so as to extend along the body shape which varies from subject to subject. As a result, the cable 20 can be secured to a desired portion of the body of the subject. Furthermore, the second portion 22 can self-retain the bent shape based on the second flexibility, and therefore an adhesive tape or an additional securing device is not required in the securement. Consequently, it is possible to enhance the degree of freedom of selection of the place where the cable 20 of the sensor 1 for detecting biological information is to be secured.

Figure 4:
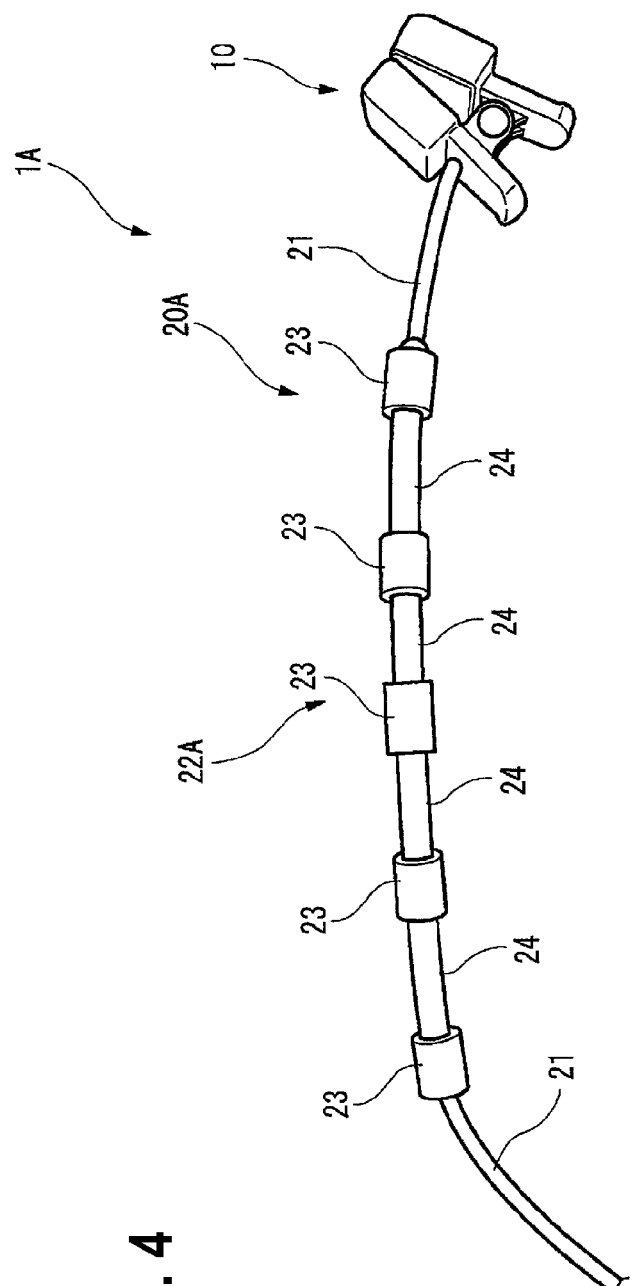
FIG. 4 is a perspective view illustrating a sensor of a second embodiment of the presently disclosed subject matter.

FIG. 4 is a perspective view illustrating a sensor 1A of a second embodiment of the presently disclosed subject matter. The components which are identical or similar to those of the sensor 1 of the first embodiment are denoted by the same reference numerals, and repeated description is omitted.

The sensor 1A of the embodiment includes the sensor body 10 and a cable 20A. The cable 20A includes the first portion 21 and a second portion 22A. The second portion 22A is disposed so as to partly cover the first portion 21. The second portion 22A has the second flexibility which has been described in connection with the first embodiment.

The second portion 22A includes large-diameter parts 23 and small-diameter parts 24. The second portion is formed so that the maximum diameter of the large-diameter parts 23 is larger than that of the small-diameter parts 24.

Figure 5:
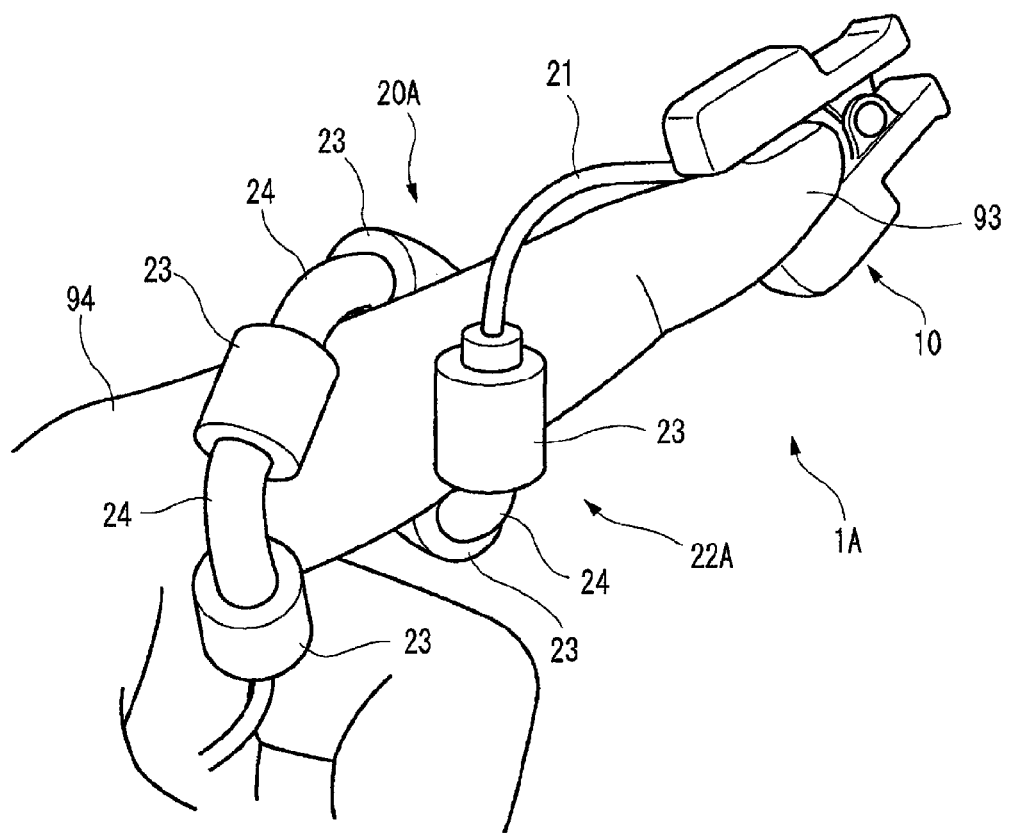
FIG. 5 is a perspective view illustrating a state where the sensor of FIG. 4 is attached to a finger of the subject.

FIG. 5 is a perspective view illustrating a state where the sensor 1A having the above-described configuration is attached to the fingertip of the subject. The sensor body 10 clamps the fingertip 93 of the subject. The second portion 22A of the cable 20A is wrapped around the finger 94. The second portion 22A is bent and deformed into a shape which spirally extends along the finger 94. The second portion 22A can retain the shape in the bent state, and therefore the state which is fitted to the finger 94 is maintained.

Figure 6:
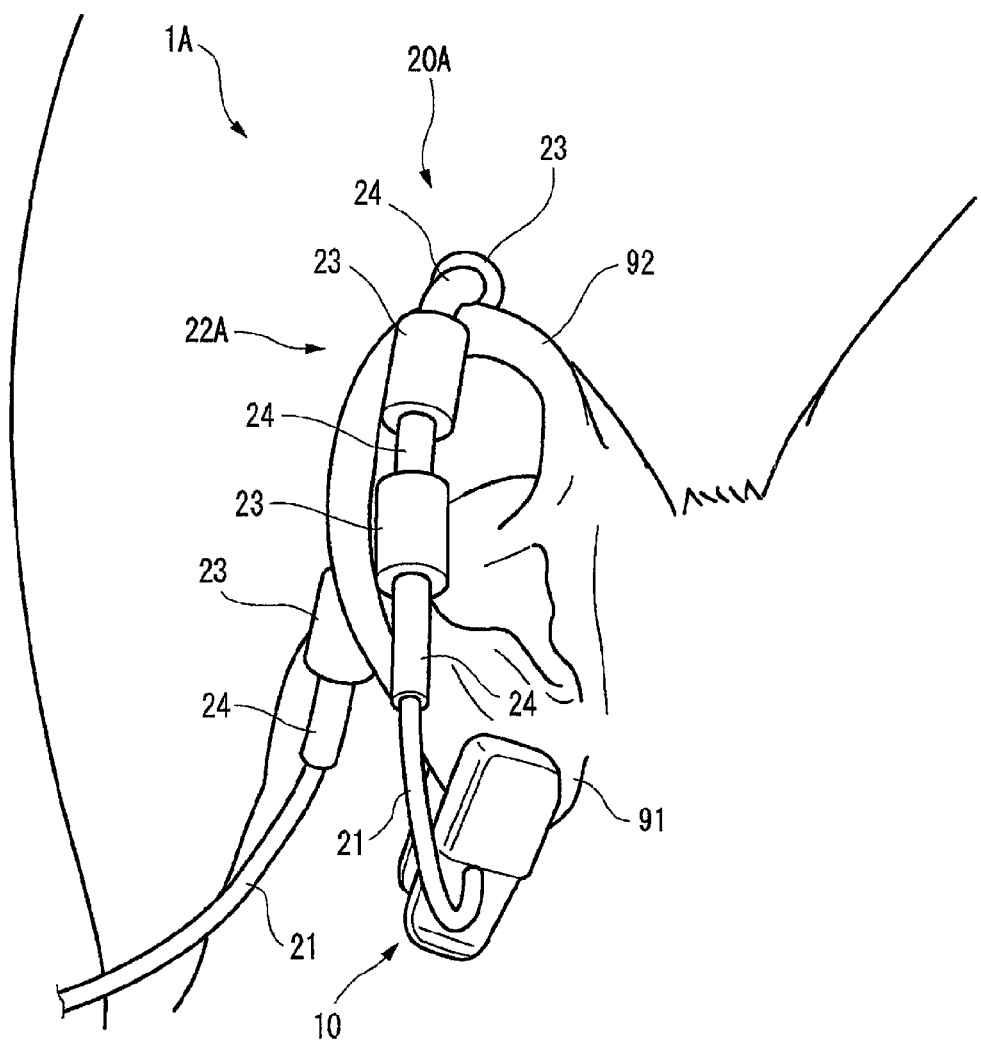
FIG. 6 is a perspective view illustrating a state where the sensor of FIG. 4 is attached to the ear of the subject.

FIG. 6 is a perspective view illustrating a state where the sensor 1A having the above-described configuration is attached to the ear of the subject. The sensor body 10 clamps the earlobe 91 of the subject. The second portion 22A of the cable 20A is hooked over the upper portion 92 of the ear. The second portion 22A is bent and deformed into a shape which extends along the upper portion 92 of the ear. The second portion 22A can retain the shape in the bent state, and therefore the state which is fitted to the upper portion 92 of the ear is maintained.

Generally, a body portion of the subject to which the second portion 22A is attached has irregular convex and concave portions. According to the configuration of the embodiment, difference in size formed between the large-diameter parts 23 and the small-diameter parts 24 can be easily caught by such irregular convex and concave portions, so that the cable 20A can be secured more surely to a body portion of the subject. Therefore, it is possible to enhance the degree of freedom of selection of the place where the cable 20A of the sensor 1A for detecting biological information is to be secured.

The large-diameter parts 23 have a third flexibility. The third flexibility is higher than the first flexibility of the first portion 21. When the large-diameter parts 23 are formed by a material such as a sponge, for example, it is possible to obtain a configuration having the third flexibility.

According to the configuration, even when the difference in size formed between the large-diameter parts 23 and the small-diameter parts 24 contact with a body portion of the subject, the burden on the skin of the subject can be suppressed. Therefore, it is possible to enhance the degree of freedom of selection of the place where the cable 20A of the sensor 1A for detecting biological information is to be secured.

FIGS. 7A to 7C are perspective views illustrating a part of a sensor 1B of a third embodiment of the presently disclosed subject matter. The components which are identical or similar to those of the sensor 1 of the first embodiment are not illustrated or are denoted by the same reference numerals, and repeated description is omitted.

As shown in FIG. 7C, the sensor 1B of the embodiment includes the sensor body 10 and a cable 20B. The cable 20B includes the first portion 21 and a second portion 22B. The second portion 22B is attachable to and detachable from the first portion 21. The second portion 22B has the second flexibility which has been described in connection with the first embodiment.

As shown in FIG. 7A, in the initial state, the second portion 22B has a plate-like appearance. When the thus configured second portion 22B is attached to the first portion 21, the second portion 22B is wrapped around a desired part of the first portion 21 as shown in FIGS. 7B and 7C. The second portion 22B is configured so as to be able to self-retain a deformed shape. Therefore, the state where the second portion is wrapped around the desired part of the first portion 21 is maintained.

According to the configuration, in accordance with the shape of a body portion of the subject to which the cable 20B is to be secured, a portion of the cable 20B in which a bent state must be retained can be arbitrarily set. Therefore, it is possible to enhance the degree of freedom of selection of the place where the cable 20B of the sensor 1B for detecting biological information is to be secured.

In this case, the second portion 22B functions as a shape retainer that is to be attached to the cable of the sensor which to be attached to a living body to detect biological information, and that retains the shape of the cable to a desired state.

FIGS. 8A to 8C are perspective views illustrating a part of a sensor 1C of a fourth embodiment of the presently disclosed subject matter. The components which are identical or similar to those of the sensor 1 of the first embodiment are not illustrated or are denoted by the same reference numerals, and repeated description is omitted.

As shown in FIG. 8C, the sensor 1C of the embodiment includes the sensor body 10 and a cable 20C. The cable 20C includes the first portion 21 and a second portion 22C. The second portion 22C is attachable to and detachable from the first portion 21. The second portion 22C has the second flexibility which has been described in connection with the first embodiment.

As shown in FIG. 8A, the second portion 22C has a body 221 which has a tubular shape in the initial state, and a slit 222 is formed over the whole length. Because of the flexibility of the body 221, the slit 222 can be expandingly opened. A core line 223 is embedded in the whole length of the body 221. The core wire 223 is configured by a metal wire or like, and has the second flexibility. The flexibility of the body 221 is higher than that of the core wire 223.

When the thus configured second portion 22C is to be attached to the first portion 21, the slit 222 is expandingly opened, and a desired part of the first portion 21 is clamped by the second portion 22C as shown in FIGS. 8B and 8C. The second portion 22C is configured so as to be able to self-retain a deformed shape. Therefore, the state where the second portion is wrapped around the desired part of the first portion 21 is maintained.

According to the configuration, in accordance with the shape of a body portion of the subject to which the cable 20C is to be secured, a portion of the cable 20C in which a bent state must be retained can be arbitrarily set. Therefore, it is possible to enhance the degree of freedom of selection of the place where the cable 20C of the sensor 1C for detecting biological information is to be secured.

In this case, the second portion 22C functions as a shape retainer that is attached to the cable of the sensor which to be attached to a living body to detect biological information, and that retains the shape of the cable to a desired state.

The embodiments have been described in order to facilitate understanding of the presently disclosed subject matter, and are not intended to limit the presently disclosed subject matter. It is a matter of course that the presently disclosed subject matter may be changed or improved without departing the spirit thereof, and includes equivalent embodiments.

In the embodiments described above, the sensor which is to be used as a probe of a pulse oximeter has been exemplarily shown. However, the presently disclosed subject matter can be applied to any adequate sensor which detects biological information, and which includes a cable transmitting a signal corresponding to the biological information.

In the second portion 22A in the second embodiment, the portions of the large-diameter parts 23 having the maximum diameter, and those of the small-diameter parts 24 having the maximum diameter are continuous over respective constant zones to form the difference in size between the large-diameter parts 23 and the small-diameter parts 24. Alternatively, the second portion 22A may have a shape in which the outer diameter is continuously increased and decreased, and large-diameter parts and small-diameter parts are repeatedly formed.

The second portion 22B in the third embodiment may be configured so as to have large-diameter parts and small-diameter parts as in the second portion 22A in the second embodiment. For example, convex and concave portions may be formed in a part of the rear side (the side which is not opposed to the first portion 21) of the plate-like second portion 22B shown in FIG. 7A, and the second portion 22B is wrapped around so that the convex and concave portions are located in the outermost circumferential surface in the state shown in FIG. 7C.

The second portion 22B in the third embodiment and the second portion 22C in the fourth embodiment are not always required to be attachable to and detachable from the first portion 21. When an adhesive portion is disposed in an adequate place, it is possible to set a state where the second portion is permanently attached to the first portion 21.

The second portion 22B in the third embodiment and the second portion 22C in the fourth embodiment are not always required to be attached to the cable of the sensor for detecting biological information. The shape retainer can be attached to an adequate cable for transmitting a signal. In a state where a cable of an electronic apparatus is bent, and secured to a desired place, for example, the shape retainer can retain the bent shape.

1, 1A, 1B: sensor
10: sensor body
20: cable
21: first portion
22, 22A: second portion
22B: second portion (shape retainer)
23: large-diameter part
24: small-diameter part

What is claimed is:

1. A sensor which is configured to be attached to a living body comprising:
   a sensor body configured to output a signal corresponding to biological information; and
   a cable configured to be connected to the sensor body and to transmit the signal,
   wherein the cable has a first portion having a first flexibility and a first-portion maximum diameter, a second portion having a second flexibility which is lower than the first flexibility, and a third portion having a third flexibility which is higher than the first flexibility,
   wherein the second flexibility enables the second portion to be bent and to retain a shape of the second portion in a bent state,
   wherein the third portion includes a large-diameter part having a third-portion maximum diameter which is larger than the first-portion maximum diameter, and
   wherein the second portion includes a small-diameter part having a second-portion maximum diameter which is smaller than the third-portion maximum diameter and larger than the first-portion maximum diameter.

2. The sensor according to claim 1, wherein the second portion is attachable to and detachable from the first portion.

3. The sensor according to claim 1, wherein the second portion having a core line which is embedded in the whole length of the second portion in a longitudinal direction of the second portion.

* * * * *